United States Patent

Makoto

Patent Number: 5,752,939
Date of Patent: May 19, 1998

[54] CATHETER FOR CONTINUOUS AMBULATORY PERITONEAL DIALYSIS

[75] Inventor: Ishizaki Makoto, Miyazaki-ken, Japan

[73] Assignee: Kabushiki Kaisha Hayashidera Medinooru, Kanazawa, Japan

[21] Appl. No.: 464,901

[22] PCT Filed: Nov. 1, 1993

[86] PCT No.: PCT/JP93/01591

§ 371 Date: Dec. 4, 1995

§ 102(e) Date: Dec. 4, 1995

[87] PCT Pub. No.: WO94/14483

PCT Pub. Date: Jul. 7, 1994

[30] Foreign Application Priority Data

Dec. 24, 1992 [JP] Japan ................. 4-357444

[51] Int. Cl.⁶ ......................................... A61M 5/32
[52] U.S. Cl. ................. 604/175; 604/29; 604/280
[58] Field of Search ........................... 604/174, 175, 604/29, 281, 280, 264

[56] References Cited

U.S. PATENT DOCUMENTS

| | | | |
|---|---|---|---|
| 4,392,855 | 7/1983 | Oreopoulos et al. | 604/29 |
| 4,687,471 | 8/1987 | Twardowski et al. | 604/29 X |
| 4,772,269 | 9/1988 | Twardowski et al. | 604/29 X |
| 5,057,075 | 10/1991 | Moncrief et al. | 604/29 X |
| 5,098,413 | 3/1992 | Trudell et al. | 604/29 X |
| 5,141,499 | 8/1992 | Zappacosta | 604/280 |
| 5,156,597 | 10/1992 | Verreet et al. | 604/175 |
| 5,322,519 | 6/1994 | Ash | 604/29 X |
| 5,380,298 | 1/1995 | Zabetakis et al. | 604/280 X |

*Primary Examiner*—Sam Rimell
*Assistant Examiner*—Luke J. Yeh
*Attorney, Agent, or Firm*—Morrison Law Firm

[57] ABSTRACT

The catheter for continuous ambulatory peritoneal dialysis includes a hypodermic tunnel portion at the intermediate portion of a tube formed with a soft biocompatable material. One leg portion of the catheter serves as an external extension. Another leg portion serves as a peritoneal cavity insertion portion having suction/drain holes. A first cuff at the boundary between the hypodermic tunnel portion and the peritoneal cavity insertion portion, the portion in the vicinity of the first cuff toward the inside of the peritoneal cavity from the first cuff is structurally such that the restoring force of the tube is enhanced. The hypodermic tunnel portion is bent in a loop form so as to take an inverse U-shape when positioned in the patient. The second cuff is disposed at the vertex of the loop. According to the method the catheter is inserted bidirectionally; in one direction through the peritoneal entry site and in the second direction hypodermally from the entrance to the skin exit in such a manner as to direct the fluid attachment end of the catheter downward. In the process the second cuff is fixed hypodermally to the fascia, and the first cuff is fixedly disposed at a position corresponding to the peritoneal entry and directing the catheter downward into the peritoneal cavity.

6 Claims, 6 Drawing Sheets

A closed system of the CAPD

CATHETER FOR CONTINUOUS AMBULATORY PERITONEAL DIALYSIS

BACKGROUND OF THE INVENTION

The present invention relates to catheters. More particularly, the present invention relates to catheters for the injection and drainage of dialysis solution during the process of continuous ambulatory peritoneal dialysis which is an effective method of hemocatharsis in chronic renal failure patients.

Use of catheters for continuous ambulatory peritoneal dialysis is known in the art. For example, continuous ambulatory peritoneal dialysis, which is a hemocatharsis for chronic renal failure patients, has been recognized by Japanese Health Insurance organizations as an effective form of hemodialysis treatment since March, 1985. Additionally, since Apr. 1, 1986, continuous ambulatory peritoneal dialysis has been approved for general practice with the only requirement being notification of the local self-governing body in the district where medical institutions are established. For these reasons, continuous ambulatory peritoneal dialysis has been put into practice at many hospitals and clinics.

The concept of continuous ambulatory peritoneal dialysis was first disclosed in the U.S. by Popovich and Moncrief in 1976. The disclosure reveals a method for continuous ambulatory peritoneal dialysis, whereby the patient carries a bag made of a soft material, such as polyvinyl chloride, in which dialysis solution is contained. The dialysis solution is connected through a tube from the soft bag into the peritoneal cavity of the patient.

This system has a distinct advantage over traditional dialysis because it allows the patient to receive dialysis while performing normal daily activities without the sense of being incapacitated.

Hemodialysis, in general, is based on the principle of allowing blood to contact a semipermeable membrane, the other side of which is in contact with an isotonic dialysis solution. Toxins, and other relatively small molecules, diffuse across the membrane until their concentration in both the dialysis solution and the blood equilabrates.

The isotonic dialysis solution is then changed to a fresh solution to permit continued purification of the blood. Solution replacement may be continuous or discontinuous. The efficiency of dialysis is directly related to many factors including, volume of dialysis fluid, number of changes of dialysis solution (or flow rate in a continuous system), length of time between changes, surface area of membrane, pore size of the membrane, rates of diffusion of the toxins, patient variables, etc.

Peritoneal hemodialysis is principled in the substitution of the natural semipermeable capillary bed membranes that are abundant within the peritoneal cavity, for the artificially provided semipermeable membranes of the hemodialysis machine. By continuously flooding the interperitoneal extravascular space with isotonic dialysis solution exchange of toxins from the blood occurs and dialysis is accomplished.

A closed system utilizing continuous ambulatory peritoneal dialysis as the fundamental principle is comprised, as shown in FIG. 1, of catheter A, catheter adapter B, made of titanium, connecting tube C, and bag D, made of polyvinyl chloride, which contains peritoneal dialysis solution. However, longstanding problems still remain with catheters used in this field.

Refering to FIG. 2, the catheter shown, for continuous ambulatory peritoneal dialysis, initially disclosed in the prior art is called a Tenckhoff type catheter. Such devices in the prior art were constructed with hypodermic tunnel portions (for example, as shown at F) provided at intermediate portions of elongated straight tubes made of silicon rubber.

One leg portion G serves as external extension, and the other leg portion H serves as peritoneal cavity insertion portion having suction/drainage holes. A first cuff I is provided at the boundary between the hypodermic tunnel portion F and the peritoneal cavity insertion portion H, and second cuff J is provided with a suitable spacing from first cuff I at the hypodermic tunnel portion F.

A disadvantage with this system is that in order to prevent tunnel infection, the exit site of external extension G is required to be directed downward. Additionally, the peritoneal cavity insertion H must also be directed downward in order to maintain the efficiency of the dialysis system when the patient is upright. Ordinarily, the implant operation is carried out whereby the straight tube is bent and fixed in an inverse U-shape. In addition to the difficulty of the operation, there is a marked tendency for the second cuff to migrate to the outside of the skin due to the resilient forces exerted by the bent portion. In view of these drawbacks in the Tenckhoff type catheters, a Swan Neck type catheter was subsequently developed.

Referring now to FIG. 3 hypodermic tunnel portion F is shown between first cuff I and second cuff J. This prior art catheter is preformed into an inverse U-shape. Such Swan Neck type catheters are widely used and have essentially replaced the Tenckhoff type catheters. Reference symbol K indicates the injection/drainage holes provided at the front end portion of the peritoneal cavity insertion portion H.

A major complication of the continuous ambulatory peritoneal dialysis is peritonitis. The aggravating factors that contribute most to the incidence of peritonitis reside in the presence and nature of the indwelling catheter. Clearly, any improvement in the catheter's biological compatibility, its shape, or techniques for it's implantation and use would dramatically decrease the incidence of related complications. Clinical studies addressing these issues have led to the identification of relevant technical problems as follows.

Conventional Swan Neck type catheters are permanently bent in an inverted U shape between cuffs. However, since this bent portion is made of a soft material such as silicon rubber, etc., there is little resistance to excessive bending and kinking of the tube. As a result, the flow in and out of the peritoneal cavity may be constrained because the tube has become confined or narrowed. To prevent such phenomenon at the time of operation, ablation of a broad connective tissue is required.

Although forming a hypodermic tunnel by trocar in loop form, immediately on the abdominal wall fascia is uncomplicated on its face, it still contsitutes a difficult manipulation. For example, in order to place the second cuff in an upper hypodermic tissue at a depth of 2 cm from the exit site, the surgeon is inevitably required to heavily ablate the tissue. This ablation creates an excessive dead cavity, resulting in a delay in healing. This problem is potentially solved by the tight sealing organization of the connective tissue to the second cuff. Unfortunately, delays in healing are rampant among prior art devices.

In addition, since the second cuff is near the exit site, infection is an inevitable result. This is compounded by the fact that the second cuff is not sutured and fixed at the time of operation lengthens the time required for healing of the exit site.

Another important factor that effects dialysis efficiency is whether drainage of the dialysis solution in the continuous ambulatory peritoneal dialysis is good or bad. However, in the case of the conventional catheter, since the resilient force on the peritoneal cavity side from the first cuff is weak, the catheter may abnormally migrate, as a result of intestinal peristaltic vermicular motion acting on the portion of the catheter within the peritoneal cavity. In addition, due to the weakness of restoring force, when unfavorable tip migration has occured, amelioration of the improper postion cannot be carried out. Clearly, these drawbacks of prior art catheters and methods employing them merit further attention.

OBJECTS AND SUMMARY OF THE INVENTION

It is therefore an object of the present invention to overcome the drawbacks of the prior art.

It is another object of the present invention provide a catheter and method using same make to make improvements over conventional catheters and prevent exit site infection or hypodermic tunnel infection.

It is still another object of the present invention to provide a catheter and method using same to dramatically decrease the incidence of peritonitis fatal to the continuous ambulatory peritoneal dialysis minimilizing complications.

Yet another object of this invention is to provide a catheter to increase the restoring force of the catheter at the beginning portion within the peritoneal cavity thus precluding tip migration of a front end portion thereof within the peritoneal cavity thereby eliminating dialysis solution drainage failure.

In order to facilitate meeting the above mentioned objects of the present invention the following features and embodiments are herein described.

According to a feature of the present invention, there is provided a catheter for continuous ambulatory peritoneal dialysis in which a hypodermic tunnel portion is provided at the intermediate portion of a tube formed of soft material having biological compatibility with the human body, one leg portion thereof serves as an external extension, the other leg portion thereof serves as a peritoneal cavity insertion portion having suction/drain holes, a first cuff is provided at a boundary between a hypodermic tunnel portion and the peritoneal cavity insertion portion, and a second cuff is provided with a suitable spacing within the hypodermic tunnel portion, the hypodermic tunnel portion is bent in the form of a half loop so that it takes an inverse U-shape, the second cuff is disposed at the vertex of the loop, and the first cuff is disposed at a position corresponding to the peritoneum.

According to a further feature of the present invention, there is provided a a catheter in which, in the catheter for continuous ambulatory peritoneal dialysis of the first embodiment, the portion in the vicinity of the first cuff toward the inside of the peritoneal cavity from the first cuff of the peritoneal cavity insertion portion in the catheter for continuous ambulatory peritoneal dialysis is of a structure and material such that the restoring force of the tube is enhanced.

Yet a further feature the present invention is directed to a catheter for continuous ambulatory peritoneal dialysis wherein the tube thickness is larger over a predetermined length of the tube toward the inside of the peritoneal cavity from the first cuff of the peritoneal cavity insertion portion, thus to enhance the restoring force.

Yet a still further feature the present invention is directed to a catheter for continuous ambulatory peritoneal dialysis wherein the second cuff of the hypodermic tunnel portion is provided at the vertex of the half loop bent in an inverse U-shape to reinforce it.

Yet another embodiment of the present invention is directed to a catheter for continuous ambulatory peritoneal dialysis wherein the hypodermic tunnel portion is bent in a half loop form so as to take an inverse U-shape, the second cuff is disposed at the vertex of the loop, the first cuff is disposed at a position corresponding to the peritoneal entrance, the first cuff is a structure and material that can be fixed on the peritoneum, and the second cuff is a structure and material that can be fixed on the abdominal rectus fascia.

Yet a still further embodiment of the present invention is a catheter having a tube with a peritoneal insertion end, a fluid connecting end, and a hypodermic tunnel region extending from a peritoneal cavity entry point to a skin exit point, the hypodermic tunnel region being defined by a semicircular loop, having an apex, the loop being formed at a predetermined distance from the peritoneal insertion end, a first cuff disposed on the hypodermic tunnel region at the peritoneal cavity entry point, a second cuff disposed on the hypodermic tunnel region, a plurality of injection and drainage channels on the peritoneal insertion end, and a means for increasing a restoring force of the hypodermic tunnel region whereby tip migration is prevented.

According to yet a still further feature of the present invention a process for facilitating injection and drainage of a dialysis solution for continuous ambulatory peritoneal dialysis is provided, comprising the steps of; providing a catheter having a tube with a peritoneal insertion end, a fluid connecting end, and a hypodermic tunnel region extending from a peritoneal cavity entry point to a skin exit point, the hypodermic tunnel region being defined by a semicircular loop, having an apex, the loop being formed at a predetermined distance from the peritoneal insertion end, a first cuff disposed on the hypodermic tunnel region at the peritoneal cavity entry point, a second cuff disposed on the hypodermic tunnel region, a plurality of injection and drainage channels on the peritoneal insertion end, and a means for increasing a restoring force of the hypodermic tunnel region whereby tip migration is prevented, incising the skin of a patient to provide at least one incision access for implanting the catheter, implanting the peritoneal insertion end into the patient, fixing the peritoneal insertion end within a first one of the at least one incision access using a cigarette suture technique, making a first hypodermal tunnel from the first one of the at least one incision access to another of the at least one incision access, threading the fluid connecting end of the catheter through the first hypodermal tunnel, making a second hypodermal tunnel from the another of the at least one incision access to a skin exit, and threading the fluid connecting end of the catheter through the second hypodermal tunnel whereby the catheter forms a tight fit in the second hypodermal tunnel.

According to even yet a still further embodiment of the present invention a process for facilitating injection and drainage of a dialysis solution for continuous ambulatory peritoneal dialysis which comprises the steps of; providing a catheter having a tube with a peritoneal insertion end, a fluid connecting end, and a hypodermic tunnel region extending from a peritoneal cavity entry point to a skin exit point, the hypodermic tunnel region being defined by a semicircular loop, having an apex, the loop being formed at a predetermined distance from the peritoneal insertion end, a first cuff disposed on the hypodermic tunnel region at the peritoneal cavity entry point, a second cuff disposed on the hypodermic tunnel region, a plurality of injection and drainage channels on the peritoneal insertion end, and a means for increasing a restoring force of the hypodermic tunnel region whereby tip migration is prevented, marking incision sites on the patient using one of the catheter and a template for marking, the incision sites corresponding to a peritoneal insertion site, and a second cuff attachment site, making a first incision at the peritoneal insertion site, whereby peritoneal entry is accomplished, inserting the peritoneal insertion end and the first cuff through the first incision, withdrawing the first cuff to align with the peritoneal insertion site, performing cigarette sutures whereby the first cuff of the catheter is fixed within the first incision, making a second incision at the second cuff attachment site whereby peritoneal wall facia exposure is accomplished, threading the fluid connecting end hypodermally through a trochar penetrated tunnel from the first incision in an upward curving direction to the second incision, whereby the second cuff aligns within the second incision, threading the fluid connecting end hypodermally through a trochar penetrated tunnel from the second incision in a downward curving direction to a skin exit site whereby the catheter is tightly form fit within the trochar penetrated tunnel, suturing the second cuff firmly within the second incision, and closing the incisions over the first and second cuffs.

The requirements for the tube in this invention is that it be formed of soft material having compatibility with the human body. A tube of silicon rubber is one example that meets these requirements. However, the invention is not limited to the use of silicon rubber. The thickness of the tube is not particularly limited as long as the human body compatibility is taken into consideration. For example, a tube having an outside diameter of from about 4.9±0.5 mm and an inside diameter of about 2.6±0.5 mm is suitable.

In addition, the cuff may be formed, for example, by winding and fixing an unwoven cloth of dacron, having the human body compatibility, onto the outer circumference of the tube. Again, any material having human body compatibility may be used as the material of the cuff. The material of the cuff is not limited to dacron.

Accordingly, it is an advantageous feature of this invention, that in a catheter for continuous ambulatory peritoneal dialysis, the hypodermic tunnel portion is bent in a loop form so as to take an inverse U-shape, and the second cuff is disposed at its loop vertex to reinforce its portion. Accordingly, it is possible to prevent isthmus of the catheter internal cavity resulting from an excessive bending at the time of operation of the hypodermic tunnel portion.

Another advantageous feature of this invention is that the second cuff is caused to be positioned at the vertex of the inverse U-shaped loop, thereby making it possible to minimize dead cavity formation following ablation of the hypodermic tissue when the hypodermic tunnel is prepared. Thus, healing organization by the connective tissue around the second cuff is not delayed and the incidence of exit site infection is significantly reduced.

Yet another advantageous feature of this invention is that in the catheter according to this invention, the portion in the vicinity of the first cuff toward the inside of the peritoneal cavity from the first cuff of the peritoneal cavity insertion portion is of a structure such that the restoring force of the tube is enhanced. Accordingly, catheter tip migration caused by the intestine movement is reduced. In addition, even if such tip migration takes place, the catheter can be easily restored to the Douglas cavity.

In yet another feature of this invention the hypodermic tunnel portion is bent in a loop form so as to take an inverted U-shape. The second cuff is disposed at the vertex of the loop, the first cuff is disposed at a position corresponding to the peritoneum, the first cuff is caused to be of a structure such that it can be fixed on the peritoneum, and the second cuff is caused to be of a structure such that it can be fixed hypodermically to the abdominal rectus fascia. Accordingly, the catheter is very securely fixed whereby healing of the wounds can be expected at an early stage.

Moreover, since down growth healing of the catheter exit site is complete earlier after the operation, patients can vigorously clean the area around the catheter and bathe sooner which results in reducing both exit site and hypodermic tunnel infections.

It is yet another feature of this invention that catheter is preformed to the shape which is to be taken at the time when implantation is completed.

It is yet another feature of the present invention that the catheter is of a structure such that it is fixed in a good stable state at two portions of the first cuff and the second cuff. Accordingly, there is seldom a drainage failure fatal to continuous ambulatory peritoneal dialysis, resulting in high reliability catheter.

It is yet another feature of the present invention to provide that a method for the implantation of the catheter of the present invention results in the insertion of the catheter into the peritoneal cavity from a first incision, the threading of the catheter hypodermically to a second incision that corresponds to the position of the cuff at the apex of the curved portion, and finally tunneling the catheter hypodermically in a downward curving direction from the second incision to exit the skin all by penetratingly separating the structure of the hypodermis whereby the catheter obtains a tight formed fit from the second incision through the skin exit.

In summary, this invention relates to improvements in a catheter and its method of implementation for injection/drainage of a dialysis solution of continuous ambulatory peritoneal dialysis which is hemocatharsis for chronic renal failure patient, and its main objectives are to allow complications such as peritonitis, etc. to be as minimized, and to reduce the effects of tip migration of the catheter within the peritoneal cavity, thus eliminating dialysis solution drainage failure.

The catheter for continuous ambulatory peritoneal dialysis is constituted as follows: A hypodermic tunnel portion is provided at the intermediate portion of a tube formed with a soft material having human body compatibility, one leg portion thereof serving as an external extension. The other leg portion serving as a peritoneal cavity insertion portion having suction/drain holes, a first cuff is provided at the boundary between the hypodermic tunnel portion and the peritoneal cavity insertion portion, the portion in the vicinity of the first cuff toward the inside of the peritoneal cavity from the first cuff is structurally such that the restoring force of the tube is enhanced, the hypodermic tunnel portion is bent in a loop form so as to take an inverse U-shape when positioned in the patient, the second cuff is disposed at the vertex of the loop.

For implementation, the catheter is inserted bidirectionally; in one direction through the peritoneal entry site and in the second direction hypodermically from the entrance to the skin exit in such a manner as to direct the fluid attachment end of the catheter downward. In the process the second cuff is fixed hypodermally to the fascia, and the first cuff is fixedly disposed at a position corresponding to the peritoneal entry in such a manner as to direct the catheter downward into the peritoneal cavity.

The above, and other objects, features and advantages of the present invention will become apparent from the following description read in conjunction with the accompanying drawings, in which like reference numerals designate the same elements.

BRIEF DESCRIPTION OF THE DRAWINGS

FIGS. 6–14 show an explanatory sequence, in succession, of the steps for a method of implanting a catheter for continuous ambulatory peritoneal dialysis of the present invention, wherein:

FIG. 6 is an explanatory view showing a skin incised (opened) portion.

FIG. 7 is a perspective view showing the step wherein the stylet is inserted through a catheter for continuous ambulatory peritoneal dialysis according to the present invention to solidify the catheter's bend it such that an angle of the front end thereof at the time of insertion becomes equal to 150 degrees.

FIG. 8 is a perspective view showing the catheter in a cigarette suture state within the peritoneum incised (opened) portion.

FIG. 9 is an explanatory view illustrating the step where the first cuff is fixed to the peritoneal fascia.

FIG. 10 is an explanatory view showing the step where the first hypodermic tunnel is made from the position of the first cuff to the position of the second cuff using a trocar.

FIG. 11 is an explanatory view showing the state where the second hypodermic tunnel from the position of the second cuff to the skin exit is made using a trocar in a manner similar to that shown in FIG. 11.

FIG. 12 is an explanatory view showing the state where the second cuff is fixed in it's hypodermic position in the fascia.

FIG. 13 illustrates cross sectionally the position of a properly implanted catheter of the present invention.

FIG. 14 is a front view illustrating the position of a properly placed implanted catheter of the present invention relative to the position of the suture wounds.

DETAILED DESCRIPTION OF THE PREFERRED EMBODIMENT(S)

Figure 1:
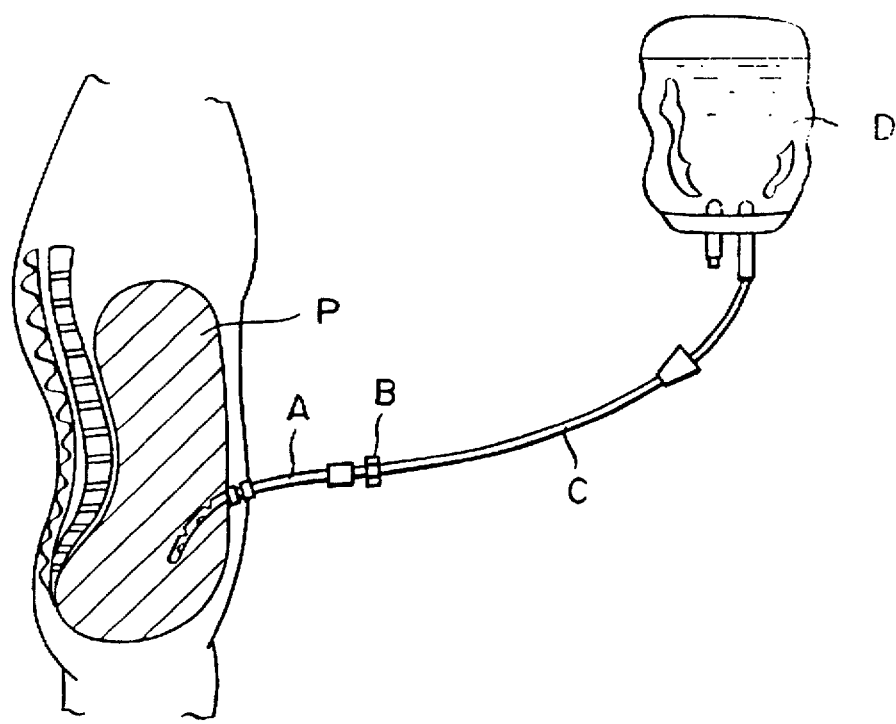
FIG. 1 is a perspective view showing a closed system for continuous ambulatory peritoneal dialysis as shown in the prior art.
Figure 2:
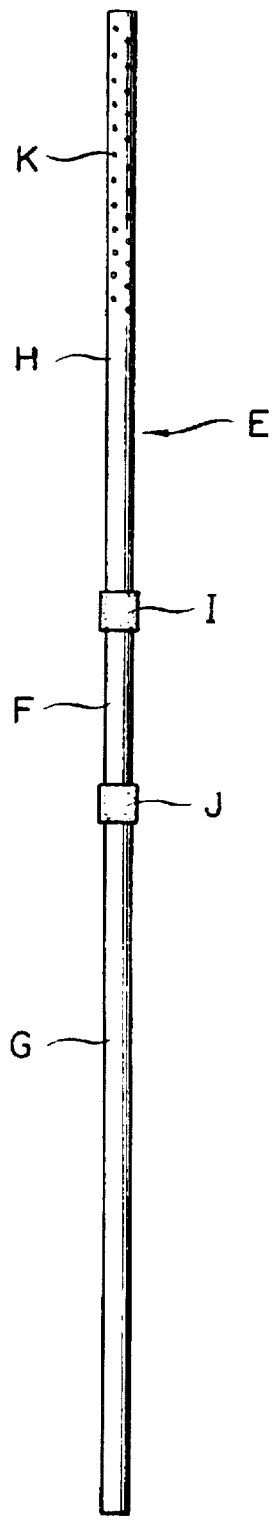
FIG. 2 is a front view of a conventional Tenckhoff type catheter, as known in the prior art.
Figure 3:
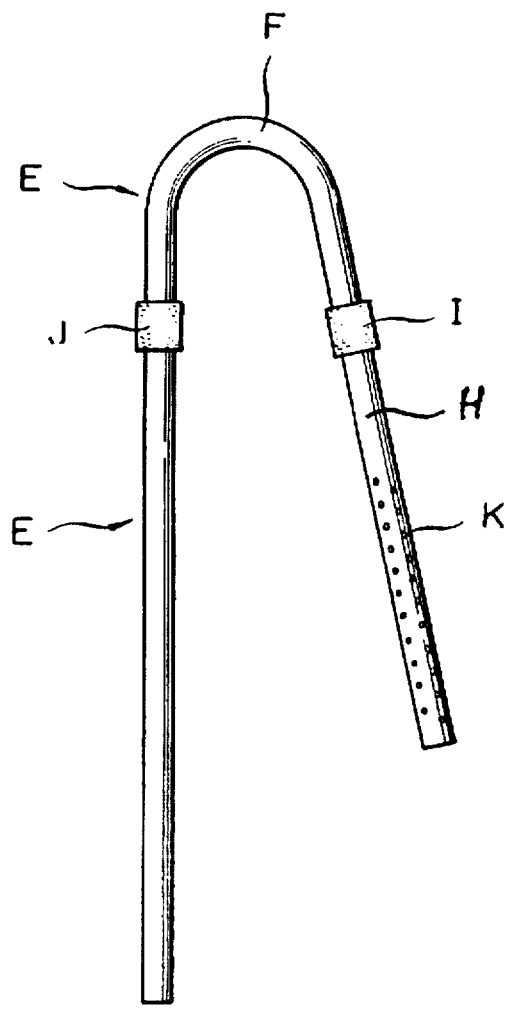
FIG. 3 is a front view of a Swan neck type catheter currently widely used among devices of the prior art.
Figure 4:
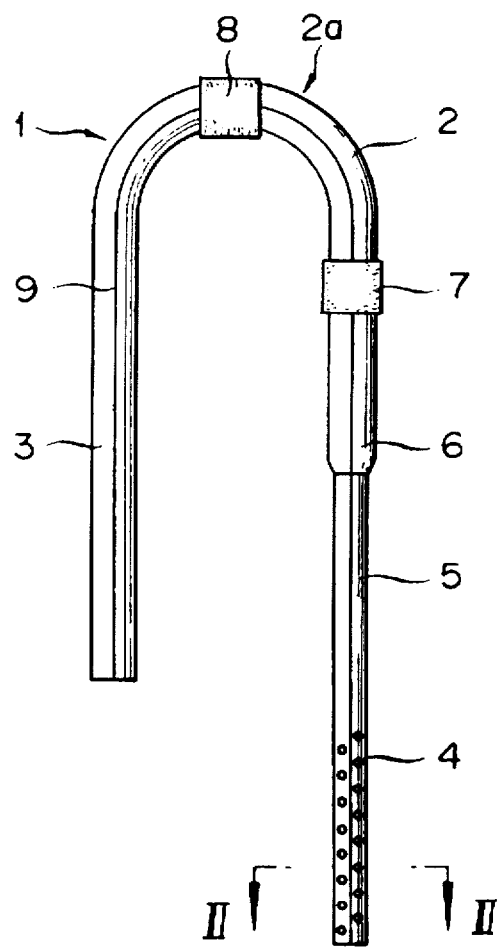
FIG. 4 is a front view showing a catheter for continuous ambulatory peritoneal dialysis of the inverse U-shape type according to the present invention.

Referring now to FIG. 4, catheter tube 1 for continuous ambulatory peritoneal dialysis according to the present invention is a tube of a soft material such as silicon rubber. At the intermediate portion of catheter tube 1, hypodermic tunnel portion 2 is provided. One leg portion of hypodermic tunnel portion 2 serves as external extension 3, and the other leg portion thereof serves as peritoneal cavity insertion portion 5 having holes for suction and drainage 4.

Silicon rubber catheter tube 1 is a transparent tube having, for example, an entire length of about 435±20 mm, with an outside diameter of about 4.9±0.5 mm, and an inside diameter of about 2.6±0.5 mm. To a portion of the circumference along the length thereof, radiopaque stripe 9, in the longitudinal axis direction, is imbedded. Peritoneal cavity insertion portion 5 is about 175±10 mm long, see also FIG. 5.

Figure 5:
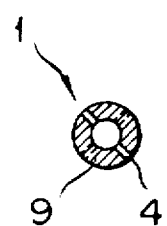
FIG. 5 is a cross sectional view taken along the line II—II in FIG. 4.

The first 85±10 mm of the end portion of peritoneal cavity insertion portion 5 distal from hypodermic tunnel portion 2 has disposed thereon a multiplicity of radially directed suction/drain holes 4 that are 0.5±0.7 mm in diameter, pass through the tubing wall, and are spaced at predetermined intervals (see also FIG. 5).

On the outer circumference of the tube at the juncture of peritoneal cavity insertion portion 5 and hypodermic tunnel portion 2, a first cuff 7 (about 10 mm) of dacron is provided. In addition, there is employed a thickening 6 such that the thickness of the tube is greater by about 6.0±0.5 mm beginning at a position of about 40±5 mm toward the inside of the peritoneal cavity from first cuff 7 of the peritoneal cavity insertion portion 5 and extending in the direction of external extension 3 so that the restoring force is enhanced.

In a direction toward the intermediate portion from first cuff 7, hypodermic tunnel portion 2 is provided. Hypodermic tunnel portion 2, has a permanently formed semi-circular loop 2a. This bending renders catheter 1 substantially inversely U-shaped as a whole. In addition, at the vertex (summit) of loop 2a, second cuff 8 (about 10 mm) of dacron is disposed.

According to preferred embodiments, the length between first cuff 7 and second cuff 8 is about 60 mm. In a direction extending from second cuff 8, external extension 3, which is about 180±20 mm in length, is formed.

A method of implanting catheter 1 of this invention is sequentially illustrated in FIGS. 6–14.

Figure 6:
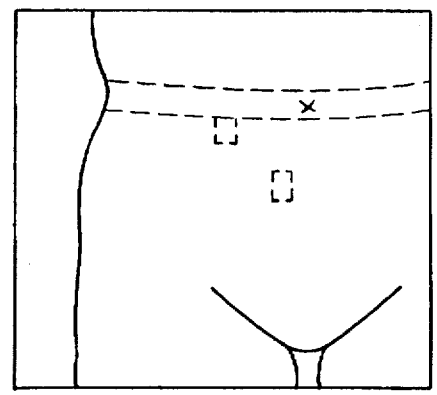

Catheter 1 or a template thereof, is placed on the abdominal wall as a means for prospectively measuring its final position. At this time, the height of the first cuff 7 is determined in such a manner that the position of a first side hole of the catheter is caused to be in correspondence with the pubic bone connective upper edge, and the first cuff 7 is then caused to be in correspondence with the center of the abdominal rectus. When the catheter has been positioned thus, the positions of the first cuff 7 and the second cuff 8 are marked to indicate the points of incision. Local anesthesia is administered and a skin incision of about 5 cm along the longitudinal axis of the first cuff 7 is made (FIG. 6).

Hypodermic fatty tissue is incised by an electric surgical knife and good hemostasis is essential. Further, the anterior sheath portion of the abdominal rectus fascia is exposed while pushing aside the fatty layer by using a hook. The fascia is then incised by 3–4 cm whereby the surgical knife enters the posterior sheath portion of the fascia without cutting the abdominal rectus by the hook.

Local infiltration anesthesia is sufficiently implemented to the peritoneal incised portion to allow a small incision of approximately 5 mm being careful so as not to injure the intestines while rasing together the posterior sheath portion of the abdominal rectus fascia and the peritoneum by using a hook pin. In preparation for inserting the catheter of the present invention, the front end of a Weston-Roberts catheter for IPD is tentatively inserted through the small incised abdominal hole into the Douglas cavity to confirm its contact.

Figure 7:
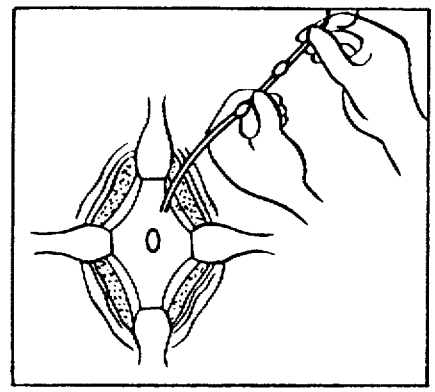

About 100 ml of physiological saline is injected through the catheter and the catheter is removed. Then, using a lubricant, a stylet is inserted into the catheter of the present invention whereby the bending angle becomes equal to about 150 degrees at the portion of the catheter that is about 5 cm from the peritoneal end (FIG. 7). The catheter front end is inserted from the small incised hole and pushed forward until it comes into contact with the right pubic bone center along the peritoneal cavity front wall. The ring portion of the stylet is gripped and is drawn from that position along the abdominal wall while externally rotating 180 degrees.

The drawing continues until resistance is suddenly lost at the entrance of the pelvis minor. The rotation is continued an additional 90 degrees, 270 degrees total, and the catheter is pushed again until first cuff 7, see FIG. 4, is just inside the peritoneal cavity. Then, the catheter is rotated so that the radiopaque white line is positioned on the rear surface side while fixing the stylet. Thereafter, the stylet is removed while holding the catheter in place.

When the catheter front end is precisely inserted into the Douglas cavity, the catheter is cleaned by injecting 10 ml of physiological saline in and out until there is no longer any resistance.

Figure 8:
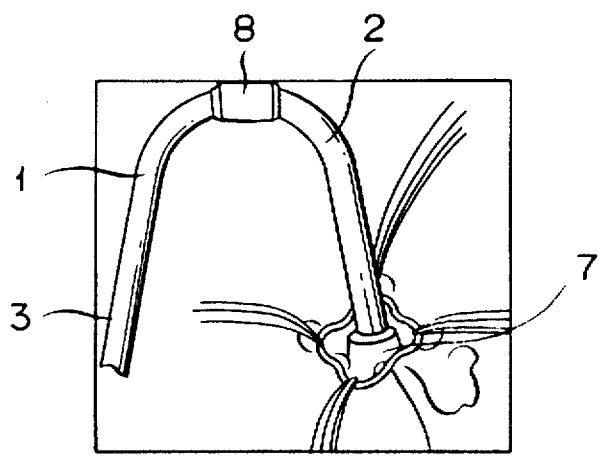
Figure 9:
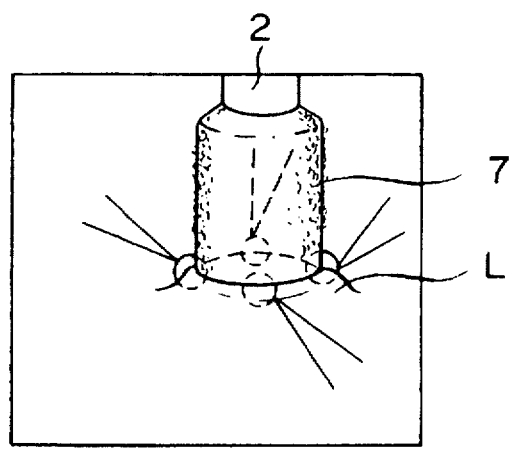

Referring now to FIG. 8, the peritoneum and the posterior fascia sheath which have been incised are together subjected to four-point support by using pearn forceps to apply cigarette sutures by using a #3-0 Dexon thread. Until this manipulation, first cuff 7 is within the peritoneal cavity. However, referring now to FIG. 9, first cuff 7 is taken out to the outside of the peritoneal cavity L to implement the cigarette suture i.e. the mouth of the opening portions is closed and the first cuff is sutured in a position that appears as a cigarette seemingly in the mouth.

In this way first cuff 7 is sutured to peritoneum L sufficiently to clamp their portions to apply tuberculation thereto to further fix it to the first cuff 7. Similarly, the peripheral portion is subjected to four-point fixing by using Dexon thread at an interval of 90 degrees to allow that portion to be in a water tight seal state. At this time point, it is confirmed by X-ray that the catheter front end is precisely positioned into the Douglas cavity.

In preparation for the next steps, a Penrose drain is divided into three portions suitable to be deployed in the vicinity of the second cuff 8 to suture the abdominal rectus fascia anterior sheath. During the subsequent manipulations, the portion of the catheter within the peritoneal cavity needs to remain directed downward at all times.

Figure 10:
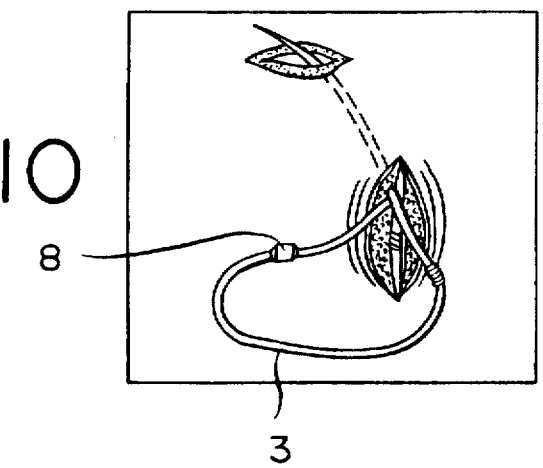
Figure 11:
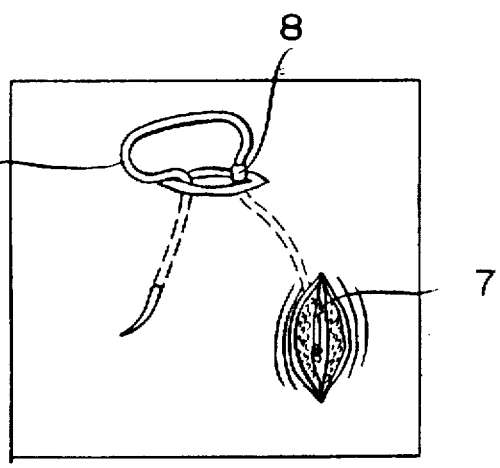
Figure 12:
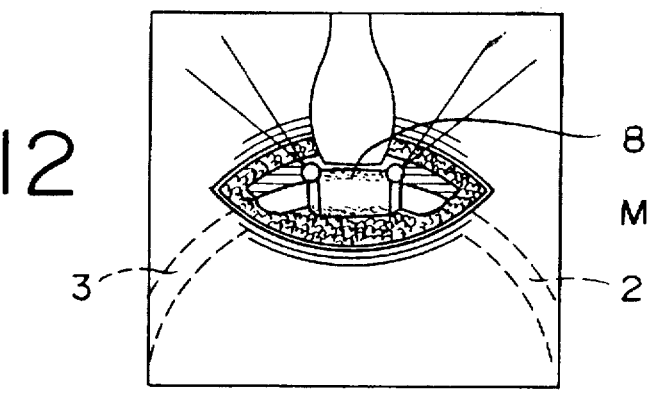

Referring now to FIG. 10, an incision of about 2 cm is made in the skin at the sight of second cuff 8, and the fatty layer is also incised by using an electric surgical knife while arresting bleeding to expose the fascia.

Immediately above the fascia, catheter 3 is passed hypodermally from the first cuff incised wound toward the second cuff incised wound using a trocar tunneler. Similarly, referring now to FIG., 11, catheter 3 is passed hypodermally in a downward direction to exit from the skin at the site 4 to 5 cm from the placement site of second cuff 8. Then, referring to FIG. 12, second cuff 8 is fixed on fascia M using a #3-0 Dexon thread with two stitches.

Figure 13:
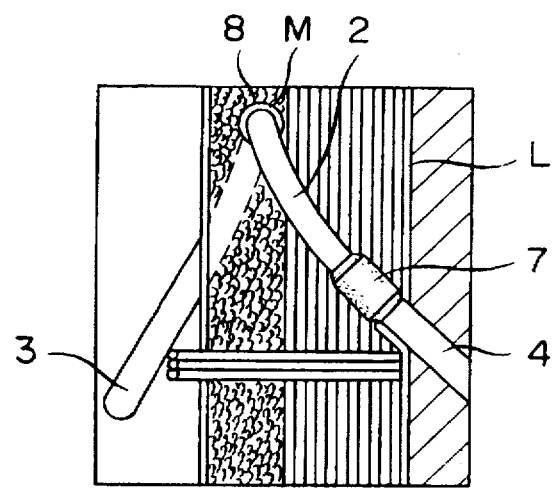
Figure 14:
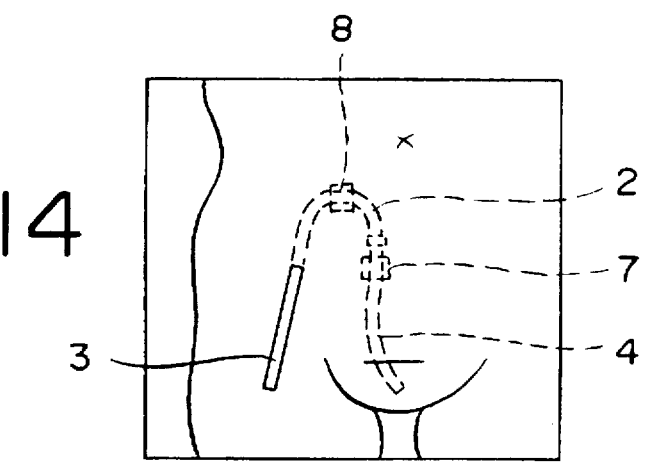

When two wounds are sutured in a manner separated into double layers to close those wounds, the catheter will have been implanted as shown in FIGS. 13 and 14. FIG. 13 is a cross sectional view after the catheter is implanted. A catheter adapter is fitted over the catheter front end portion outside the human body to connect a connecting tube thereto to start continuous ambulatory peritoneal dialysis. The solution, 1 liter of 1.5% dianeal solution is changed six times daily.

The results of a study conducted to determine the frequency of complication comparing the conventional catheter and the catheter of the present invention for continuous ambulatory peritoneal dialysis is shown in Table 1. This present invention reduced frequencies of the permanent catheter tip migration to $1/12$, exit site infection to $1/4$, tunnel infection to $1/2$, and peritonitis to $1/4$ of the conventional type catheter.

Namely, peritonitis has a low frequency of once a month with respect to 91.4 patients. In addition, all the catheters of this invention are functioning properly. As compared to the prior art, continuous ambulatory peritoneal dialysis could be carried out in a more safe manner.

In a follow-up study, the number of study cases of continuous ambulatory peritoneal dialysis using the catheter according to the third embodiment was 60. The total observation (cumulative) period being 1359 months. The results of study, showing the categorized numbers of complications which occurred during the observation period is shown in Table 2.

From this result, it is seen that frequency of complication has been further reduced. Table 1 A comparison between complications of the catheter of this invention and complications of the conventional catheter.

|  | Catheter of this invention | Conventional catheter |
| --- | --- | --- |
| No. of cases | 37 | 32 |
| Ratio between man and woman (man:woman) | 27:10 | 22:9 |
| Observation period (patient month) | 457 | 465 |
| Permanent catheter tip migration (patient-month) | 1 (1/457) | 12 (1/38.8) |
| Exit site infection (patient-month) | 3 (1/152.3) | 13 (1/35.8) |
| Tunnel infection (patient-month) | 3 (1/152.3) | 6 (1/77.5) |
| Peritonitis (patient month) | 5 (1/91.4) | 21 (1/22.1) |
| Catheter function failure (patient-month) | 0 | 11 (1/42.3) |

Table 2 shows result of cumulative period (patient-month) 1359 months with respect to 60 patients using this invention.

|  | No. of cases | Case rate (patient-year) |
| --- | --- | --- |
| Permanent catheter tip migration | 6 | 0.05 |
| Exit site infection | 17 | 0.15 |
| Tunnel infection | 12 | 0.11 |
| Peritonitis | 34 | 0.30 |
| Catheter replacement | 3 | 0.03 |

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A catheter comprising:
   a tube having a peritoneal insertion end and a fluid connecting end;

said tube having a hypodermic tunnel region extending from a peritoneal cavity entry point to a skin exit point;

said hypodermic tunnel region being defined by a semicircular loop having a permanently formed apex, said loop being formed at a predetermined distance from said peritoneal insertion end;

a first cuff disposed on said hypodermic tunnel region at said peritoneal cavity entry point;

a second cuff disposed on said hypodermic tunnel region;

said peritoneal insertion end having a plurality of injection and drainage channels; and said hypodermic tunnel region having a means for increasing a restoring force whereby tip migration is prevented;

said means for increasing a restoring force including increasing a wall thickness of said tube in said hypodermic tunnel region.

2. The catheter of claim 1 wherein:

said means for increasing a restoring force includes increasing a wall thickness of said tube in said hypodermic tunnel region; and said second cuff is disposed on said apex of said hypodermic tunnel region.

3. The catheter of claim 1, further comprising:

a wall embedded radiopaque strip embedded longitudinally in said tube whereby said catheter can be detected by x-ray.

4. A process for facilitating injection and drainage of a dialysis solution for continuous ambulatory peritoneal dialysis, comprising the steps of:

a. providing a catheter having a tube with a peritoneal insertion end, a fluid connecting end, and a hypodermic tunnel region extending from a peritoneal cavity entry point to a skin exit point, said hypodermic tunnel region being defined by a semicircular loop, having an apex, said loop being formed at a predetermined distance from said peritoneal insertion end, a first cuff disposed on said hypodermic tunnel region at said peritoneal cavity entry point, a second cuff disposed on said hypodermic tunnel region, a plurality of injection and drainage channels on said peritoneal insertion end, and a means for increasing a restoring force of said hypodermic tunnel region whereby tip migration is prevented;

b. incising the skin of a patient to provide at least one incision access for implanting said catheter;

c. implanting said peritoneal insertion end into said patient;

d. fixing said peritoneal insertion end within a first one of said at least one incision access using a cigarette suture technique;

e. making a first hypodermal tunnel from said first one of said at least one incision access to another of said at least one incision access;

f. threading said fluid connecting end of said catheter through said first hypodermal tunnel;

g. making a second hypodermal tunnel from said another of said at least one incision access to a skin exit; and h. threading said fluid connecting end of said catheter through said second hypodermal tunnel whereby said catheter forms a tight fit in said second hypodermal tunnel.

5. A process for facilitating injection and drainage of a dialysis solution for continuous ambulatory peritoneal dialysis, comprising the steps of:

a. providing a catheter having a tube with a peritoneal insertion end, a fluid connecting end, and a hypodermic tunnel region extending from a peritoneal cavity entry point to a skin exit point, said hypodermic tunnel region being defined by a semicircular loop, having an apex, said loop being formed at a predetermined distance from said peritoneal insertion end, a first cuff disposed on said hypodermic tunnel region at said peritoneal cavity entry point, a second cuff disposed on said hypodermic tunnel region, a plurality of injection and drainage channels on said peritoneal insertion end, and a means for increasing a restoring force of said hypodermic tunnel region whereby tip migration is prevented;

b. marking incision sites on a patient using one of said catheter and a template for marking, said incision sites corresponding to a peritoneal insertion site, and a second cuff attachment site;

c. making a first incision at said peritoneal insertion site, whereby peritoneal entry is accomplished;

d. inserting said peritoneal insertion end and said first cuff through said first incision;

e. withdrawing said first cuff to align with said peritoneal insertion site;

f. performing cigarette sutures whereby said first cuff of said catheter is fixed within said first incision;

g. making a second incision at said second cuff attachment site whereby peritoneal wall facia exposure is accomplished;

h. threading said fluid connecting end hypodermally through a trochar penetrated tunnel from said first incision in an upward curving direction to said second incision, whereby said second cuff aligns within said second incision;

i. threading said fluid connecting end hypodermally through a trochar penetrated tunnel from said second incision in a downward curving direction to a skin exit site whereby said catheter is tightly form fit within said trochar penetrated tunnel;

j. suturing said second cuff firmly within said second incision; and k. closing said incisions over said first and second cuffs.

6. The catheter of claim 1, wherein said wall thickness of said tube is increased by about 6.0±0.5 mm in said hypodermic tunnel region at a point about 40±5 mm from said first cuff toward said peritoneal insertion point.

* * * * *